US010048173B2

(12) United States Patent
Jun et al.

(10) Patent No.: US 10,048,173 B2
(45) Date of Patent: Aug. 14, 2018

(54) APPARATUS FOR ANALYTE SAMPLING, METHOD OF ANALYTE SAMPLING AND ANALYTE SAMPLING ANALYSIS SYSTEM

(71) Applicant: NVISANA CO., LTD., Yongin-si (KR)

(72) Inventors: Pil-kwon Jun, Yongin-si (KR); Yong-ik Sung, Yongin-si (KR)

(73) Assignee: NVISANA CO., LTD., Yongin-si, KG (KR)

( * ) Notice: Subject to any disclaimer, the term of this patent is extended or adjusted under 35 U.S.C. 154(b) by 237 days.

(21) Appl. No.: 14/893,640

(22) PCT Filed: May 27, 2014

(86) PCT No.: PCT/KR2014/004742
§ 371 (c)(1),
(2) Date: Nov. 24, 2015

(87) PCT Pub. No.: WO2014/193155
PCT Pub. Date: Dec. 4, 2014

(65) Prior Publication Data

US 2016/0109335 A1 Apr. 21, 2016

(30) Foreign Application Priority Data

May 28, 2013 (KR) ........................ 10-2013-0060157

(51) Int. Cl.
*G01N 1/10* (2006.01)
*G01N 1/38* (2006.01)
(Continued)

(52) U.S. Cl.
CPC ................. *G01N 1/26* (2013.01); *G01N 1/10* (2013.01); *G01N 1/2202* (2013.01); *G01N 1/38* (2013.01);
(Continued)

(58) Field of Classification Search
CPC .......... G01N 1/10; G01N 1/2202; G01N 1/26; G01N 1/38; G01N 2001/002;
(Continued)

(56) References Cited

U.S. PATENT DOCUMENTS 6,427,526 B1 * 8/2002 Davison ................. B01D 15/12 210/656
6,761,056 B2 7/2004 Schram et al.
(Continued)

FOREIGN PATENT DOCUMENTS

JP 10-253509 A 9/1998
JP 11-037909 A 2/1999
(Continued)

OTHER PUBLICATIONS

International Search Report, PCT/KR2014/004742, dated Jul. 31, 2014, including English translation, 7 pages.

*Primary Examiner* — Randy Gibson
*Assistant Examiner* — Gedeon M Kidanu
(74) *Attorney, Agent, or Firm* — Daly, Crowley, Mofford & Durkee, LLP

(57) ABSTRACT

Disclosed are an apparatus for analyte sampling, and a method of analyte sampling and an analyte sampling analysis system using the same. The apparatus includes a spray unit to receive a trapping solution and an analyte sample, and to mix and spray the analyte sample and the trapping solution of an aerosol state together, a spray chamber to provide a space to primarily trap an analyte material, which is contained in the analyte sample, in the trapping solution of the aerosol state, a trapping tube to secondarily trap the analyte material, which is not trapped in the spray chamber, by receiving the analyte sample and the trapping solution in the aerosol state from the spray chamber and mixing the trapping solution with the analyte sample, a trapping container to receive the trapping solution having the analyte
(Continued)

material trapped therein through the trapping tube, and a sample transfer unit to feed purge gas into the trapping container to transfer the trapping solution having the analyte material trapped therein to an analysis unit through a sample transfer line by the purge gas.

6 Claims, 5 Drawing Sheets

(51) Int. Cl.
*G01N 1/22* (2006.01)
*G01N 1/26* (2006.01)
*G01N 33/00* (2006.01)
*G01N 1/40* (2006.01)
*G01N 1/00* (2006.01)

(52) U.S. Cl.
CPC ... *G01N 33/0036* (2013.01); *G01N 2001/002* (2013.01); *G01N 2001/2217* (2013.01); *G01N 2001/387* (2013.01); *G01N 2001/4066* (2013.01)

(58) Field of Classification Search
CPC ..... G01N 2001/2217; G01N 2001/387; G01N 2001/4066; G01N 33/0036
See application file for complete search history.

(56) References Cited

U.S. PATENT DOCUMENTS

| | | | | |
|---|---|---|---|---|
| 7,964,029 | B2* | 6/2011 | Fogelman | B01D 11/0203 137/171 |
| 8,327,725 | B2* | 12/2012 | Kanomata | B01D 11/0203 422/512 |
| 2001/0042714 | A1* | 11/2001 | Gjerde | B01D 15/366 210/634 |
| 2002/0144949 | A1* | 10/2002 | Berger | B01D 11/0203 210/656 |
| 2003/0165941 | A1* | 9/2003 | Gjerde | B01D 15/366 435/6.12 |
| 2005/0227363 | A1* | 10/2005 | Hwang | H01L 21/02057 436/73 |
| 2006/0160239 | A1* | 7/2006 | Lee | G01N 21/314 436/164 |
| 2012/0103073 | A1* | 5/2012 | Bystron | G01N 30/34 73/61.53 |
| 2012/0262178 | A1* | 10/2012 | Dourdeville | G01N 24/08 324/321 |

FOREIGN PATENT DOCUMENTS

| | | |
|---|---|---|
| JP | 2002-328073 A | 11/2002 |
| KR | 10-1999-0005926 | 2/1999 |
| KR | 10-2000-0056635 A | 9/2000 |
| KR | 10-2002-0029197 | 5/2002 |

* cited by examiner

APPARATUS FOR ANALYTE SAMPLING, METHOD OF ANALYTE SAMPLING AND ANALYTE SAMPLING ANALYSIS SYSTEM

CROSS REFERENCE TO RELATED APPLICATIONS

This application is a U.S. National Stage of PCT application PCT/KR2014/004742 filed in the Korean language on May 27, 2014, entitled "APPARATUS FOR ANALYTE SAMPLING, METHOD OF ANALYTE SAMPLING AND ANALYTE SAMPLING ANALYSIS SYSTEM," which claims priority to Korean application 10-2013-0060157, filed on May 28, 2013, which applications are each hereby incorporated herein by reference in their entireties.

TECHNICAL FIELD

The present invention relates to an analyte sampling apparatus, an analyte sampling method, and an analyte sampling analysis system, and more particularly to an analyte sampling apparatus capable of more rapidly and quantitatively analyzing an analyte material contained in air, high-purity gas, chemical gas, and a liquid analyte sample, and an analyte sampling method and an analyte sampling analysis system using the same.

BACKGROUND ART

Air, high-purity gas, chemical gas and the like may include metals and metallic compound which may exert harmful influences on a human body. In addition, when the atmosphere or a variety of gases included in the metal and the metallic compound are used in a laboratory or a manufacturing site, the experimental result may be failed or the manufactured article may be detected.

In particular, it is generally known in the art that the contamination of an extremely small amount of metal and metallic compound, which are contained in the air of a fabrication environment and process gas, may cause severe failures such as a pattern defect or a circuit short under the environment of for example, a semiconductor fabrication process where cleanliness must be maintained. Accordingly, the states of the fabrication environment and the process gas must be thoroughly managed by rapidly monitoring the extremely small amount of contaminated metal or metal compound. However, there is no device to monitor the metal and the metal compound contained in the air and the process gas in real time or in substantially real time due to problems, such as a technical limitation and an economical aspect in measuring the extremely small amount of metal or metal compound.

According to a conventional technology of measuring metal and metallic compound, since the metal and the metal compound are measured using equipment, such as ICP-MS, or AAS, in a laboratory after sampled by a passive sampler, such as a filter, an impinge, or a wafer, for a long time and being subject to a pre-treatment, significant long time is taken until data are acquired after the sampling. Accordingly, the conventional technology has the limitations when applied to the monitoring of an industrial site or the monitoring of environmental pollution so that the environment may not be improved, or the contamination may not be previously prevented.

Particularly, according to a conventional sampling method, since a significant small amount of metal and metallic compound are contained in the air, a long time of 24 hours to 96 hours is required to sample metal and metallic compounds to the extent of obtaining a meaningful experimental result. In addition, since a complex pre-treatment process must be performed to analyze a sample filter in addition to the trapping process, time and manpower may be significantly wasted. Further, the reliability of data may be degraded as a sample is contaminated through the long-time sampling, the complex pre-treatment process, and the analysis process. Additionally, an analyzer, such as HPIC, or ICP-MS to analyze an extremely amount of a sample is mainly high-priced equipment. Accordingly, actually, after sampling at several points, samples are transferred to one analyzer to be sequentially monitored. In particular, since the fabrication line of a semiconductor or a display is in a large scale, so that the samples must be transferred to the analyzer at the distance of several tens to hundreds of meters, the conventional sampling method may not be easily employed in the field.

The conventional method of measuring the metal and the metallic compound contained in the air has the most fatal disadvantage in that monitoring may not be rapidly performed due to the long-time sampling process. Although the rapid sampling and measuring, that is, the real-time monitoring is significantly required to manage FAB concentration or manage air quality under a general environment, such as yellow dust, in the case of a semiconductor clean room, the real-time monitoring is impossible according to the conventional methods.

Many studies and efforts have been performed to solve the problems. According to a gas diffusion denuder among them, an amount of gas may be increased and the gas may be concentrated. However, since pre-treatment is significantly complex, and sampling is performed for several hours, the variation in the concentration of the gas in a measurement place may not be easily measured, and thus the above problems are not overcome.

Korea Patent Application No. 10-1999-0005926 (entitled "Gas Diffusion Scrubber", hereinafter, referred to as cited reference 1) discloses a technology of concentrating a solution within a shorter period of time. However, in the case of the cited reference 1, the sampling efficiency is rapidly varied depending on the measurement concentration, and the measurement efficiency is varied depending on the temperature and the humidity, that is, various surrounding conditions. Thus, the metering is significantly difficult. Additionally, since the sampling efficiency is varied depending on the flow rate of gas passing through a diffusion scrubber, the gas must be sampled at a low flow rate. Furthermore, since the efficiency is not uniform depending on conditions, calibration is performed using a gas standard device. Moreover, a gas sample may be additionally contaminated or lost when moving to a long distance. If a sample transfer tube is contaminated, the cleaning of the sample transfer tube may be difficult, so that the tube may be replaced with new one.

Korean Patent Application No. 10-2002-0029197 (entitled "Sampling method of Ammonia Gas with High Efficiency and Monitoring Method of Ammonia Gas", hereinafter referred to as cited reference 2) discloses an apparatus for not only sampling the ammonia gas at the high efficiency, but monitoring an amount of the ammonia gas in real time by solving the above problem. However, according to the cited reference 2, although gas is sampled only using a normal-temperature absorption solution at a normal temperature, the absorption solution has a low pH, so that the sampling of the acid gas may not be difficult.

Additionally, when a conventional monitoring apparatus for analyzing a sample is applied to a semiconductor or display fabrication line, the scale of the semiconductor or display fabrication line is increased, so that the transfer of the collected sample to an analyzer at a distance of several tens or hundreds of meters may be difficult. Furthermore, a gas sample may be additionally contaminated or lost when moving to a long distance. If a sample transfer tube is contaminated, the cleaning of the sample transfer tube may be difficult, so that the tube may be replaced with new one.

DISCLOSURE OF THE INVENTION

Problem to be Solved

The present invention is made by keeping in mind the above problems occurring in the related art, and an object of the present invention is to provide an analyte sampling apparatus capable of more efficiently sampling an analyte material from an analyte sample in a gas or liquid phase by employing a spray and a trapping tube, and an analyte sampling method using the same.

An object of the present invention is to provide an analyte sampling apparatus capable of more effectively secondarily sampling an analyte material without the contamination of the analyte sampling apparatus by draining out a cleaning solution through lines, through which the analyte material of the analyte sampling apparatus passes, after the analyte material is sampled and the cleaning solution is supplied to the trapping container, and an analyte sampling method.

An another object of the present invention is to provide an analyte sampling analysis system capable of analyzing a sample in real time by receiving the sample from the analyte sampling apparatus while maintaining analysis cleanliness by employing the analyte sampling apparatus.

Technical Solution

In order to accomplish the above objects, according to one embodiment of the present invention, there is provided an analyte sampling apparatus including a spray unit to receive a trapping solution and an analyte sample, and to mix and spray the analyte sample and the trapping solution of an aerosol state together, a spray chamber to provide a space to primarily trap an analyte material, which is contained in the analyte sample, in the trapping solution existing of the aerosol state, a trapping tube to secondarily trap the analyte material, which is not trapped in the spray chamber, by receiving the analyte sample and the trapping solution in the aerosol state from the spray chamber and mixing the trapping solution with the analyte sample, a trapping container to receive the trapping solution having the analyte material trapped therein through the trapping tube, and a sample transfer unit to feed purge gas into the trapping container to transfer the trapping solution having the analyte material trapped therein to an analysis unit through a sample transfer line by the purge gas.

In example embodiments, the analyte sample may include process gas, exhaust gas, and contaminated air of a semiconductor or a display, and may be liquid.

In example embodiments, the analyte sampling may further include a bubbler provided at one end of the trapping tube to form the trapping solution, which is fed into the trapping container through the trapping tube, in the bubble state.

In example embodiments, the analyte sampling apparatus may further include a cooling unit to cool the trapping container and the trapping tube to more easily trap the analyte material, which is not trapped, in the trapping solution.

In example embodiments, the analyte sampling apparatus may further include a cleaning unit including a cleaning solution feeding unit to feed a cleaning solution into the trapping container to remove a remaining contaminant from the trapping container, and a draining unit to drain out the cleaning solution after the trapping container is cleaned.

In example embodiments, the analyte sampling apparatus may further include a level sensor to send an alarm signal to a control unit of the analyte sampling apparatus by measuring a level of the trapping solution fed into the trapping container.

In example embodiments, the analyte sampling apparatus may further include a trapping solution circulating and feeding unit to feed the trapping solution having the analyte material trapped therein and received in the trapping container into the spray unit so that the analyte material contained in the analyte sample is concentrated and trapped.

In order to perform sampling using the analyte sampling apparatus according to example embodiments of the present invention, the first step is performed to primarily trap an analyte material, which is contained in an analyte sample, in a trapping solution of an aerosol state by mixing and spraying a predetermined amount of the trapping solution and the analyte sample of the aerosol state using a spray unit. Subsequently, the second step is performed to secondarily trap the analyte material in the trapping solution by mixing the trapping solution with the analyte material, which is not trapped, in a trapping tube. Next, the third step is performed to trap the trapping solution having the analyte material secondarily trapped therein in a trapping container. Thereafter, a trapping solution having the analyte material finally trapped therein into an analysis unit is fed to the analysis unit through a sample feeding line.

In the analyte sampling method according to example embodiments, when the analyte sample is in a gas phase, the first and third steps are repeated at least one time, so that the analyte material is trapped in to the trapping solution as much as possible. In detail, when the analyte sample is in the gas phase, after step 3), the steps of tertiarily trapping an analyte material contained in an analyte sample in the trapping solution of the aerosol state by mixing and spraying a predetermined amount of the analyte sample newly fed and the trapping solution having the analyte material secondarily trapped therein using the spray unit, quaternarily trapping the analyte material in the trapping solution by mixing the analyte sample with the aerosol-state trapping solution having the analyte material tertiarily trapped therein in a trapping tube, and trapping the trapping solution having the analyte material quarternily trapped therein in the trapping container are repeated at least one time.

In example embodiments, the analyte sampling method may further include a step of draining the analyte sample fed into the trapping container when the analyte sample is in the gas phase.

In example embodiments, the analyte sampling method may further include the steps of cleaning the trapping container by feeding a cleaning solution into the trapping container to remove a remaining contaminant from the trapping container, and draining out the cleaning solution received in the trapping container through the sample feeding line, before the first step is performed.

According to example embodiments of the present invention, there is provided an analyte sampling analysis system including a sampling receiving unit to receive the sample from the analyte sampling apparatus, an interface unit including a sample introducing unit or a calibration sample introducing unit to receive the sample from the analyte sampling apparatus and to feed a predetermined amount of a sample into an analysis unit, the analysis unit to receive the predetermined amount of the sample from the interface unit and to analyze a type and a content of an analyte material contained in the sample, and a control unit to control operations of elements of the analyte sampling apparatus and the interface unit and an operation of the analysis unit.

In the analyte sampling analysis system according to example embodiments, the interface unit may further include a sample receiving unit having a space to primarily receive the sample therein from the analyte sampling apparatus, a sample introducing unit having a space to receive the predetermined amount of the sample such that the predetermined amount of the sample received in the sample receiving unit is fed into the analysis unit, a pressure supplying unit to supply pressure to receive the sample in the sample introducing unit or pressure to inject the sample received in the sample introducing unit to the analysis unit, and a cleaning unit including a cleaning solution feeding unit to feed a cleaning solution into the sample receiving unit such that the sample receiving unit is cleaned when the sample is introduced into the analysis unit, and a draining unit to drain out the cleaning solution a and the sample remaining in the sample receiving unit after the sample receiving unit is cleaned.

In the analyte sampling analysis system according to example embodiments, the interface unit may further include a sample receiving unit having a space to primarily receive the sample from the analyte sampling apparatus, a calibration sample introducing unit including a sample introducing unit and a standard solution introducing unit to feed a predetermined amount of a sample, which is received in the sample receiving unit, into the analysis unit and to feed a standard solution for performing calibration of the analysis unit, respectively, and a cleaning unit including a cleaning solution feeding unit to feed a cleaning solution into the sample receiving unit such that the sample receiving unit is cleaned when the sample is introduced into the analysis unit, and a draining unit to drain out the cleaning solution or a sample remaining in the sample receiving unit after the sample receiving unit is cleaned.

Effect of the Invention

As described above, according to the analyte sampling apparatus of the present invention, the analyte material can be more effectively trapped from the analyte sample existing in the gas or liquid phase in real time by employing the spray and the trapping tube.

In addition, after more effectively collecting a sample regardless of the type of the sample, such as a gas sample or a liquid sample, as compared with an analyte sampling apparatus according to the related art, the sample can be transferred to the analysis unit to be automatically analyzed, so that real-time analyzing and monitoring are possible.

Further, according to the analyzing method using the analyte sampling apparatus having the above configuration, as the cleaning process is performed to clean the inner part of the analyte sampling apparatus, when the next sampling process is performed and then a sample is analyzed in the analysis unit, the sample is not contaminated, so that the analysis sensitivity for the sample can be more improved.

Moreover, according to the analyte sampling analysis system of the present invention, the sample can be more effectively concentrated to be collected using the analyte sampling apparatus, and a predetermined amount of a sample can be transferred to the analysis unit through the interface unit placed at the distance of about 100 m within 60 sec., so that the analyte material contained in the sample can be analyzed and monitored in real time.

DETAILED DESCRIPTION OF THE INVENTION

Figure 1:
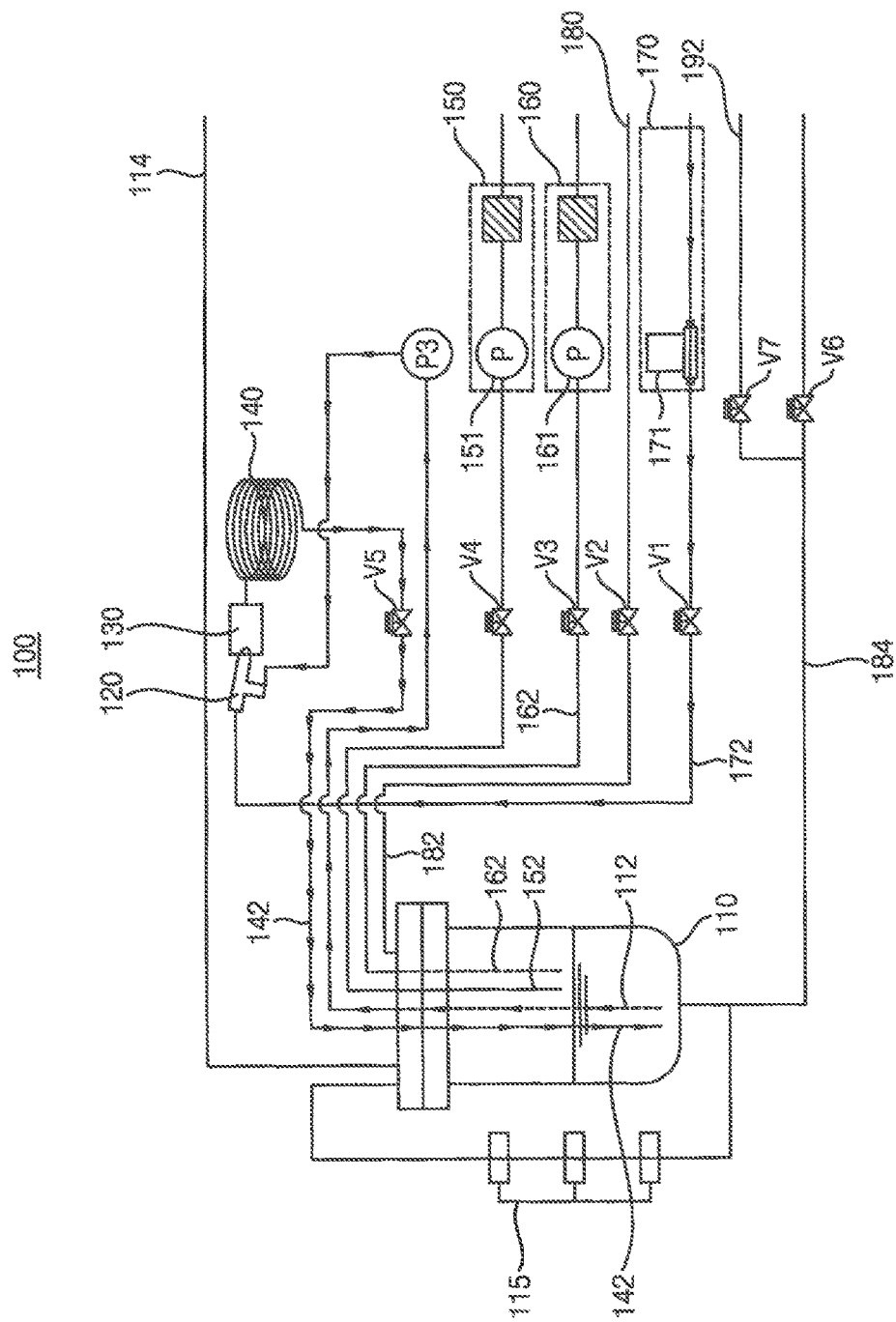
FIG. 1 is a schematic view showing an analyte sampling apparatus according to one embodiment of the present invention.

Hereinafter, an analyte sampling apparatus, an analyte sampling method, and an analyte sampling analysis system according to example embodiments will be described in detail with reference to accompanying drawings. The present invention may, however, be embodied in many different forms and should not be construed as limited to the example embodiments set forth herein and shown in accompanying drawings. It should be understood that all modification, equivalents, or alternatives of these embodiments are included within the scope of the present inventive concept. In the following description with reference to accompanying drawings, like reference numerals will be assigned to like elements. In the drawings, the sizes and relative sizes of structures and regions may be exaggerated for clarity.

It will be understood that, although the terms first, second, etc. may be used herein to describe various elements, these elements should not be limited by these terms. These terms are only used to distinguish one element from another element. Thus, a first element could be termed a second element, and the second element could be termed the first element without departing from the teachings of the present inventive concept.

The terminology used herein is for the purpose of describing particular example embodiments only and is not intended to be limiting of the present invention. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Analyte Sampling Apparatus

FIG. 1 is a schematic view showing an analyte sampling apparatus according to an embodiment of the present invention.

Referring to FIG. 1, an analyte sampling apparatus 100 according to the present invention includes an analyte sample introducing unit 170 to feed an analyte sample, a trapping solution feeding unit 160 to feed a trapping solution into a trapping container, a spray unit 120 to receive the trapping solution and the analyte sample and to mix and spray the trapping solution and the analyte sample together in an aerosol state, a spray chamber 130 to provide a space to primarily trap an analyte material, which is contained in the analyte sample, in the trapping solution existing in the aerosol state, a trapping tube 140 to secondarily trap the analyte material, which is not trapped in the spray chamber, by receiving the analyte sample and the trapping solution existing in the aerosol state from the spray chamber and mixing the trapping solution and the analyte sample together, a trapping container 110 to receive the trapping solution having the analyte material trapped therein through the trapping tube, and a sample transfer unit 180 to feed purge gas into the trapping container to transfer the trapping solution having the analyte material trapped therein to an analysis unit through a sample transfer line 184 by the purge gas.

The analyte sample introducing unit 170 according to the present invention has a structure in which an analyte sample containing an analyte material to be analyzed may be fed into the spray unit through an analyte sample feeding line 172 using a metering pump or a flow meter 171. The analyte sample feeding line 172 is provided therein with a gate valve V to be open only when the analyte sample moves into the spray unit.

As an example, the analyte sample may include semiconductor process gas, semiconductor exhaust gas, or contaminated air, and the analyte material contained in the analyte sample may include metal, metallic ions, or organic compound. As another example, the analyte sample may be a liquid applied to a semiconductor process, a biotechnology field, or various industrial fields.

The trapping solution feeding unit 160 has a structure in which the trapping solution stored in a storage unit is fed into the trapping container 110, which has been completely cleaned, through a first trapping solution feeding line 162 using a first pump 161. The first trapping solution feeding line 162 is provided therein a gate valve V1 to be open only when the trapping solution is fed into the trapping solution receiving unit 110.

The spray unit 120 receives the trapping solution fed from the trapping solution feeding unit 160 through the trapping solution receiving unit and the analyte sample fed from the analyte sample introducing unit 170, and mixes and sprays the analyte sample and the trapping solution in the aerosol state together into the spray chamber 130. In this case, the spray unit makes the trapping solution in the form of a fine drop inside the spray chamber, so that the analyte material contained in the analyte sample may be more easily mixed with and absorbed into the trapping solution in the aerosol state. In other words, the spray unit has a feature that the analyte material contained in the analyte sample is primarily trapped in the trapping solution in the aerosol state.

The spray chamber 130 is interposed between the spray unit 120 and the trapping tube 140 to provide a space where the analyte sample and the trapping solution may be sprayed in the aerosol state by the spray unit and a space where the analyte material contained in the analyte sample is primarily trapped in the trapping solution existing in the aerosol state.

The trapping tube 140 is a micro-coil tube to receive the analyte sample and the trapping solution in the aerosol state from the spray chamber 130, and to mix the analyte sample and the trapping solution in the aerosol state together while the analyte sample and the trapping solution in the aerosol state pass through the inner part of the trapping tube, so that the analyte material, which is not trapped in the spray chamber, is secondarily trapped in the trapping solution. The trapping tube 140 is formed in the shape of a non-linear passage to increase an opportunity of bringing the analyte material and the trapping solution into contact with each other, so that the analyte material may be more excellently trapped in the trapping solution. Although accompanying drawings show that the trapping tube 140 has the shape of a trapping coil, the trapping tube 140 need not be formed in the shape of a spiral coil, but formed in various shapes sufficient to allow an absorbent to more effectively meet the atmosphere. In other words, the trapping tube 140 may have a non-linear shape instead of the spiral shape, and the present invention is not limited to the shape of the trapping tube 140 shown in the drawings.

The trapping tube 140 has a structure of being connected with the trapping container through a second trap line 142, and the second trap line 142 may be provided therein with a gate valve V5 to be open only when the trapping solution having the analyte material of the analyte sample trapped therein is fed into the trapping container.

The trapping container 110 has a space to receive a trapping solution and a space to receive a trapping solution having an analyte material trapped therein through the spray unit, the spray chamber, and the trapping tube. For example, the trapping container has a cap to seal the trapping container, and a structure of being mechanically coupled to the spray unit through first trap line 112 passing through the cap. The first trap line 112 may be provided therein with a circulating pump P3 to supply pressure so that the trapping solution or the trapping solution having the analyte material trapped therein may be fed into the spray unit.

Additionally, the trapping container 110 has a structure of being connected with the second trap line 142 having one end provided closely to the bottom surface of the trapping container through the cap thereof. The second trap line 142 may be provided therein with the gate valve V5 so that the trapping solution or the trapping solution having the analyte material of the analyte sample trapped therein may be fed into the trapping container. As another example, the trapping container 110 is connected with a plurality of feeding lines to selectively receive a trapping solution, a cleaning solution, purge gas and a trapping solution having an analyte material trapped therein through the feeding lines, respectively. The amounts of materials to be fed into the trapping container may be adjusted by selectively opening/closing gate valves provided in the feeding lines, respectively.

As an example, the trapping container 110 receives both of the analyte sample and the trapping solution which are drained from the trapping tube 140. In this case, when the analyte sample is gas, the trapping solution is gathered to a lower portion of the trapping container 110 by gravity while the analyte sample, which is gas, is gathered to an upper portion of the trapping container. The upper and lower portions of the trapping container have lines to drain the analyte sample, which is gas, and the trapping solution, respectively. In other words, the analyte sample, which is gas, is drained through an upper draining line 114 positioned above the trapping container, and the trapping solution having the analyte material absorbed therein is drained through a sample transfer line positioned under the trapping container.

In this case, since the analyte material (including metal and metallic compound) contained in the analyte sample is trapped in the trapping solution while passing through the spray unit, the spray chamber, the trapping tube 140, the analyte material is rarely contained in the drained analyte sample, and the trapping solution has an analyte material (metal and metallic compound) originally contained in the analyte sample. Thus, the analyte material is drained out of the analyte sampling apparatus if the sampling of the analyte material is finished after the analyte material has been trapped in the trapping container.

The sample transfer unit 180 feeds the purge gas into the trapping container through a purge gas feeding line 180 to transfer the trapping solution having the analyte material trapped therein to the analysis unit (not illustrated) through the sample transfer line 184 by the fed purge gas. Here, the sample transfer unit serves a purge gas feeding unit, and the sample transfer line 184 mechanically couples the lower portion of the trapping container and the analysis unit to each other. The purge gas allows the trapping solution to be fed into the analysis unit, which is far away from the sample transfer unit, along with the purge gas without the loss of the trapping solution when the trapping solution is fed to the analysis unit through the sample feeding line. The sample feeding line may be provided therein with a gate valve V6 to be open only when the trapping solution having the analyte material trapped therein is fed into the analysis unit along with the purge gas.

As an example, the analyte sampling apparatus 100 according to the present invention includes the first trap line 112 connected with the trapping container to feed the trapping solution received in the trapping container into the spray unit, the second trap line 142 to feed the trapping solution having the analyte material trapped therein into the trapping container via the spray unit, the spray chamber, and the trapping coil through the first trap line 112, and the circulating pump P3 to circulate the trapping solution having the analyte material trapped therein through the first and second trap lines so that the analyte material may be concentrated and trapped.

In this case, the circulation pump is provided on the first trap line, the gate valve V5 provided in the second trap line 142 is open, and gate valves V1 to V4, V6, and V7 provided in other lines, respectively, are close. The number of times of circulating the trapping solution to concentrate and trap the analyte material may be properly determined by an experimenter depending on the type of the analyte material to be trapped or an average amount of the analyte material to be trapped.

The analyte sampling apparatus 100 according to the present invention may further include level sensors 115 to send an alarm signal to a control unit (not illustrated) by measuring the level of the trapping solution fed into the trapping container.

As another example, the analyte sampling apparatus 100 according to the present invention may include a cooling unit (not illustrated) to cool the trapping container 110 and the trapping tube 140 so that an analyte material, which is not trapped in the trapping solution, may be more easily trapped in the trapping solution. The cooling unit may be a cooling coil to surround outer portions of the trapping container and the trapping tube.

As still another example, the analyte sampling apparatus according to one embodiment of the present invention may further include a bubbler provided at one end of the second trap line 142 connected with the trapping tube to form the trapping solution, which is fed into the trapping container through the second trap line, in the bubble state. The bubbler may include a membrane having micro-holes.

As still another example, the analyte sampling apparatus according to one embodiment of the present invention may include a cleaning solution feeding unit 150 to feed a cleaning solution through a cleaning solution feeding line 152 in order to clean an analyte material remaining in the trapping container and lines, and a draining unit to drain the cleaning solution to the outside through a draining line 192 after cleaning the trapping container and the lines.

More specifically, the cleaning solution fed from the cleaning solution feeding unit may be drained out through the draining line 192 after passing through the trapping container, the first trap line, the spray unit, the spray chamber, the trapping coil, the second trap line, the trapping container, and the sample transfer line 184. The draining line may be provided therein with a gate valve V7 to be open only when the cleaning solution is drained.

The analyte sampling apparatus having the above-described configuration may more effectively sample the analyte material from the analyte sample in a gas or liquid phase in real time by applying the spray and the trapping tube, and may secondarily sample the analyte material without the contamination of the analyte sampling apparatus by draining out the cleaning solution through lines, through which the analyte materials of the analyte sampling apparatus pass, after the analyte material is sampled and the cleaning solution is supplied to the trapping container.

In addition, according to the present invention, when the analyte sample is in a gas phase, the trapping solution is circulated in the analyte sampling apparatus having the above elements, so that concentration and sampling are consecutively performed. Therefore, different from the conventional technology of performing sampling for a long term or applying pressing conditions to sample the analyte material contained in a trapping solution in a measurable amount, the concentration and the sampling can be performed without limitations in environments or conditions. As a result, according to the present invention, the analyte sample may be significantly usefully employed even in the measuring of high-purity gas or chemical gas as well as typical air.

Meanwhile, the analyte sampling apparatus having the above configuration can dilute a highly-concentrated sample to have a desirable concentration and feed the sample into the analysis unit.

Furthermore, the analyte sampling apparatus having the above configuration can secure samples, which are broadly distributed, at an analysis work time point to efficiently and clearly transfer the sample to the analysis unit which is far away from the analyte sampling apparatus.

Figure 2:
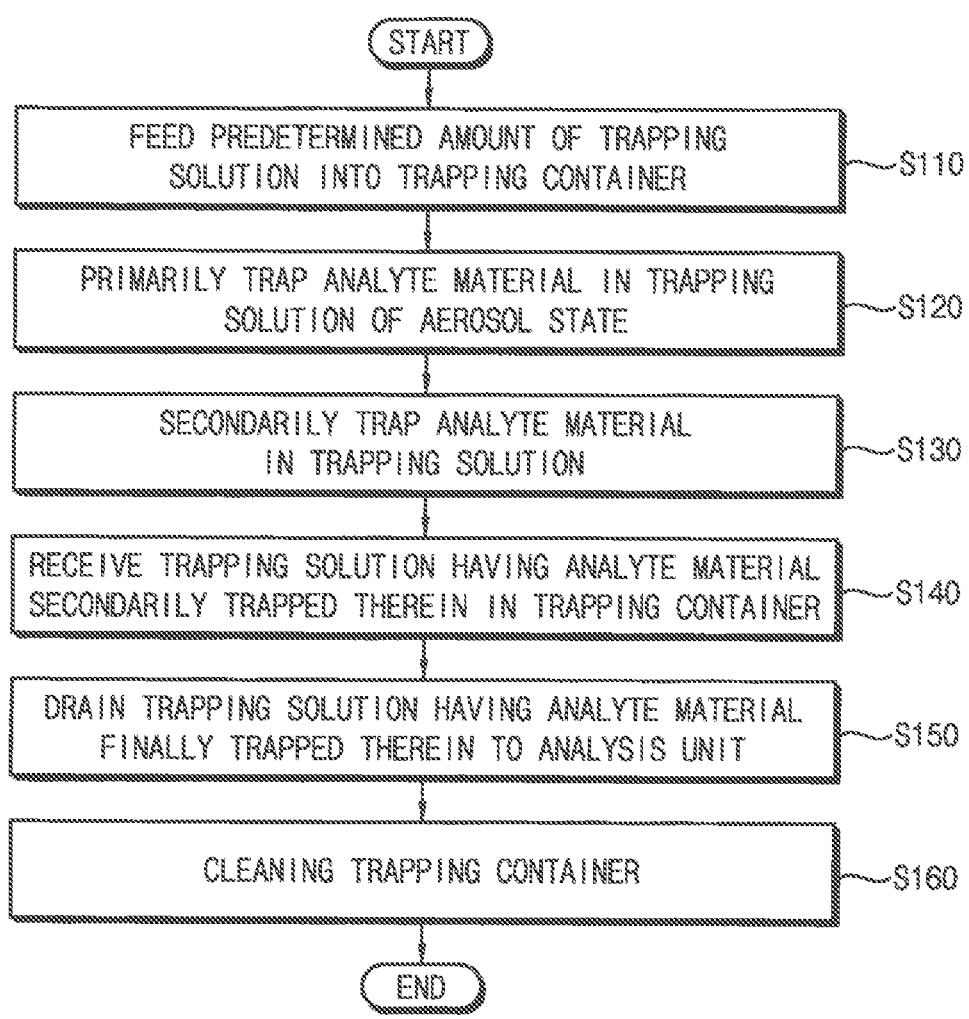
FIG. 2 is a process flowchart to explain an analyte sampling method using the analyte sampling apparatus.

FIG. 2 is a process flowchart to explain an analyte sampling method using the analyte sampling apparatus shown in FIG. 1.

Referring to FIG. 2, a predetermined amount of a trapping solution is fed into a trapping container (step S110).

In step S110, the trapping solution received in the trapping solution storage unit is fed into the trapping container 110 completely cleaned through the first trapping solution feeding line 162 after actuating the first pump P1 and opening the gate valve V3.

Then, the analyte material contained in the analyte sample is primarily trapped in the trapping solution existing in the aerosol state by mixing and spraying the analyte sample and the trapping solution in the aerosol state using the spray unit (step S120).

To primarily trap the analyte material in step S120, the trapping solution and the analyte sample are simultaneously fed into the spray unit. In this case, the trapping solution received in the trapping container 110 is fed into the spray unit through the first trap line by actuating the circulating pump. The analyte sample received in the analyte sample introducing unit is fed into the spray unit through the analyte sample feeding line 172 by the operation of the metering pump. The analyte sample and the trapping solution fed into the spray unit are sprayed in the aerosol state into the spray chamber by the spray unit, and the trapping solution in the aerosol state is increased in the contact area with the analyte sample, so that the analyte material may be more easily mixed with and absorbed in the trapping solution in the aerosol state. In other words, the analyte material is absorbed in the trapping solution within the shorter period of time, thereby performing the primary trapping.

Next, the analyte material is secondarily trapped in the trapping solution by mixing the analyte sample and the trapping solution having the analyte material primarily trapped therein and existing in the aerosol state together (step S130).

According to the secondary trapping of the analyte material in step S130, the analyte sample and the trapping solution pass through the non-linear passage of the trapping tube 140 while the trapping solution in the aerosol state is formed to a trapping solution in a liquid phase, and the opportunity of bringing the analyte material and the trapping solution into contact with each other and mixing the analyte material and the trapping solution together is increased, so that the analyte material may be secondarily trapped in the trapping solution.

Then, the trapping solution having the analyte material secondarily trapped therein and the analyte sample are fed and trapped into the trapping container (step S140).

In step S140, the trapping solution and the analyte sample may be trapped in the trapping container as the trapping solution having the analyte material secondarily trapped therein and the analyte sample are fed into the trapping container through the second trap line.

According to an analyte sampling method according to example embodiments, when the analyte sample is in a gas phase, a predetermined amount of an analyte sample is separately fed through the analyte sample feeding unit, and the first step to the third step are repeated at least one time using the trapping solution having the analyte material trapped therein, so that the analyte material may be trapped in the trapping solution as much as possible.

Specifically, when the analyte sample is in the gas phase, after step 3), repetition is performed at least one time with respect to the steps of tertiarily trapping the analyte material contained in the analyte sample in the trapping solution existing in the aerosol state by mixing and spraying a predetermined amount of an analyte sample newly received from the analyte sample feeding unit and the trapping solution in step S140 using the spray unit, quaternarily trapping the analyte material in the trapping solution having the analyte material tertiarily trapped therein and existing in the aerosol state by mixing the analyte sample and the trapping solution together in the trapping tube, and trapping the trapping solution having the analyte material quaternarily trapped therein in the trapping container.

Additionally, the analyte sampling method according to the embodiments may further include a step of draining out the gas-phase analyte sample fed into the trapping container through the trapping tube when the analyte sample is in the gas phase.

Next, the trapping solution having the analyte material finally trapped therein is fed into the analysis unit via the sample feeding line using the purge gas (step S150).

In this case, the purge gas allows the trapping solution to be fed into the analysis unit, which is far away from the sample transfer unit, along with the purge gas without the loss of the trapping solution when the trapping solution is fed to the analysis unit through the sample feeding line.

After step S150, the analyte sampling method may further include the step (S160) of cleaning the trapping container by feeding the cleaning solution into the trapping container to clean the contaminant remaining in the trapping container and a step of draining out the cleaning solution received in the trapping container through the sample feeding line.

As another example, the cleaning of the trapping container and the draining of the cleaning solution may be performed before the step S110 of feeding a predetermined amount of a trapping solution into the trapping container, thereby ensuring the cleanliness of the analyte sampling apparatus.

According to the analyte sampling method, the analyte material from the analyte sample in a gas or liquid phase may be more effectively sampled in real time by applying the spray and the trapping tube, and may be secondarily sampled without the contamination of the analyte sampling apparatus by draining out the cleaning solution through lines, through which the analyte materials of the analyte sampling apparatus pass, after the analyte material is sampled and the cleaning solution is supplied to the trapping container.

Analyte Sampling Analysis System

FIG. 3 is a block diagram schematically showing an analyte sampling analysis system including the analyte sampling apparatus according to the present invention.

Referring to FIG. 3, an analyte sampling analysis system 500 according to one embodiment of the present invention includes at least one analyte sampling apparatus 100, an interface unit 200 that includes a sample receiving unit to receive a sample therein from the analyte sampling apparatus, and feeds the sample received in the sample receiving unit into an analysis unit, the analysis unit 300 that receives a predetermined amount of a sample through the interface unit to analyze the type of an analyte material contained in the sample and the content of the sample, and a control unit 400 that controls the operations of elements constituting the analyte sampling apparatus and the interface unit. As an example, although the analyte sampling apparatus constituting the analyte sampling analysis system may be arranged in a position different from or the same as that of the analysis unit, the whole system may be operated through one control unit.

At least one analyte sampling apparatus is applied to the analyte sampling analysis system, and has a structure of including the trapping solution feeding unit 160, the spray unit 120, the spray chamber 130, the trapping tube 140, the trapping container 110, a sample transfer unit 180 to transfer the sample to the analysis unit through a sample transfer line 184, and the cleaning solution feeding unit 150, similarly to the analyte sampling apparatus shown in FIG. 1. Since the details of the analyte sampling apparatus is described in detail with reference to FIG. 1, the details thereof will be omitted in the following description in order to avoid redundancy. As an example, when two analyte sampling apparatuses may be applied to the analyte sampling analysis system, the first analyte sampling apparatus may perform the sampling for an analyte sample in a gas phase, and the second analyte sampling apparatus performs the sampling for an analyte sample in a liquid phase.

The interface unit 200 includes a sample receiving unit to receive an analyte sample (trapping solution having an analyte material trapped therein) secured from at least one analyte sampling apparatus 100 and a sample introducing unit to receive a predetermined amount of a sample fed from the sample receiving unit. The interface unit 200 alternately receives samples from the sample introducing unit to feed the samples to the analysis unit at a distance of several tens to hundreds of meters, so that the samples may be sequentially fed to the analysis unit. Hereinafter, the details of the interface unit will be described with reference to FIG. 4.

The analysis unit 300 receives the predetermined amount of the sample (trapping solution having the analyte material trapped therein) through the interface unit to measure the type and the content of the analyte material existing in the sample. For example, the analysis unit 300 may include HPIC, ICP-MS, ICP-AES, AAS, HPLC, CE, UV-vis, or Fluorescence.

The control unit 400 may be a unit installed therein with a program to control the operations of elements constituting the analyte sampling apparatus 100, to control the operations of elements constituting the interface unit 200, and to control the analysis of the analysis unit 300.

As another example, although not shown, the analyte sampling apparatus 100 may be applied to a main unit including both of the interface unit 200, the analysis unit 300, and the control unit 400 for use.

The analyte sampling analysis system having the above configuration not only may have an effective transfer system capable of transferring the sample to the analysis unit at a long distance of several tens to hundreds of meters, but may prevent the sample from being additionally contaminated or lost when the sample is moved to a long-distance place. Further, the analyte sampling analysis system may receive a new sample from the sample receiving unit of the interface unit during the analyzing of the sample so that time taken to analyze and monitor the sample may be reduced.

Figure 3:
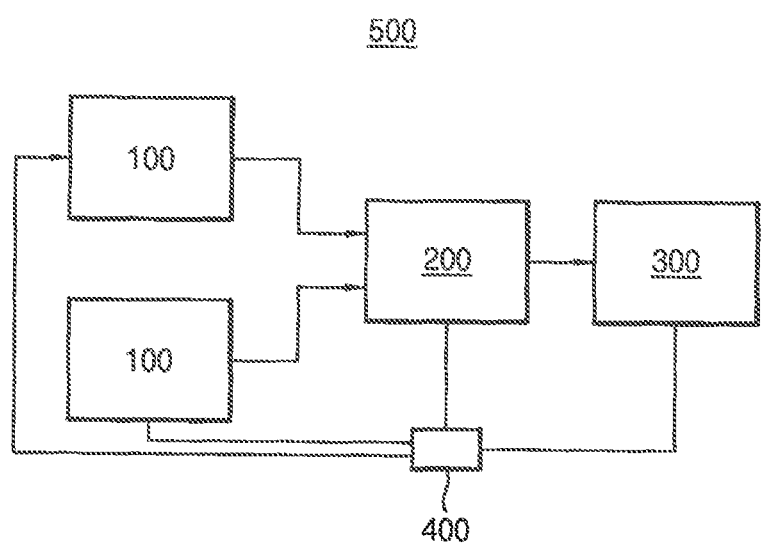
FIG. 3 is a block diagram schematically showing an analyte sampling analysis system including the analyte sampling apparatus according to the present invention.
Figure 4:
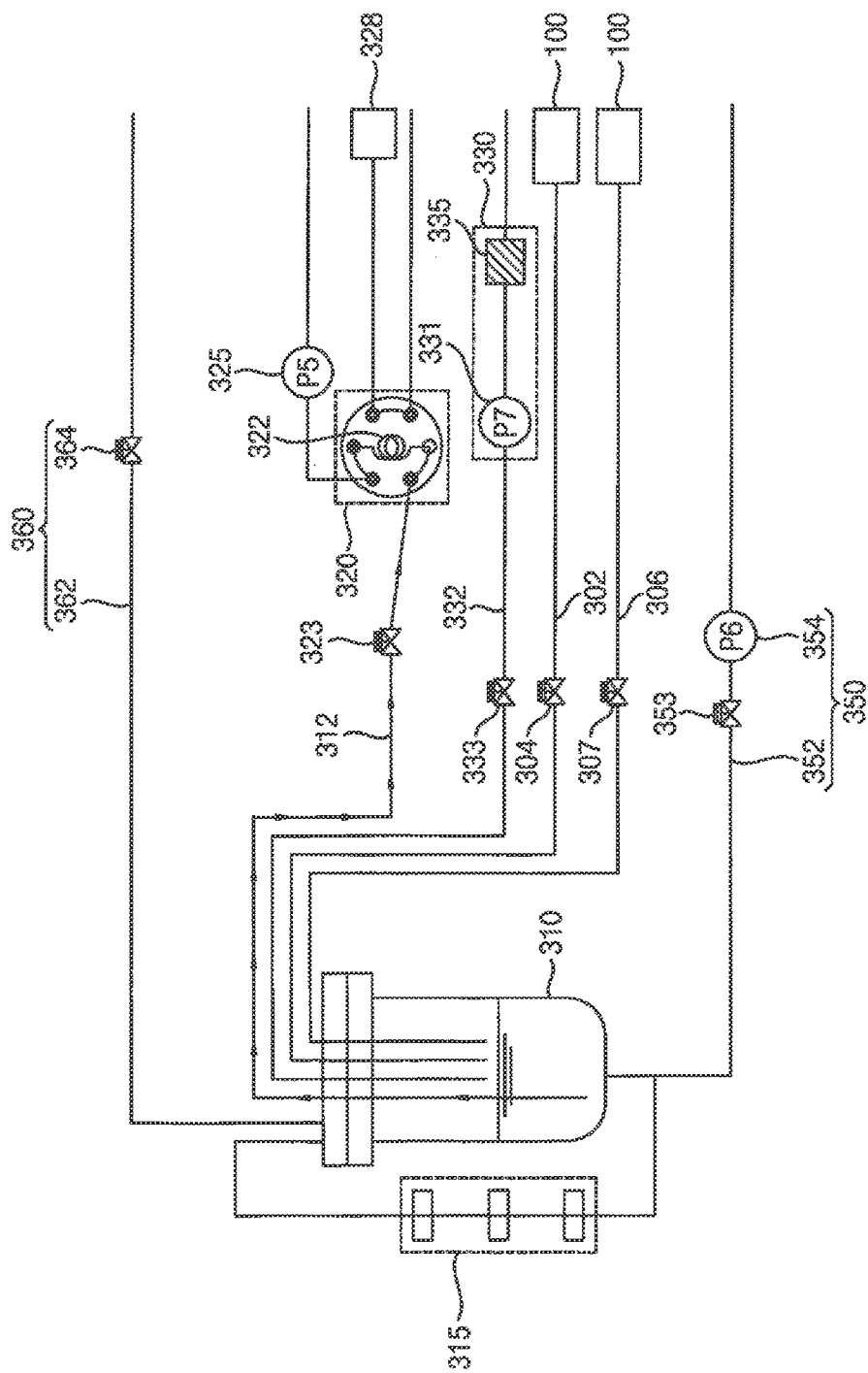
FIG. 4 is a schematic view showing an interface unit applied to the analyte sampling analysis system in FIG. 3.

FIG. 4 is a schematic view showing the interface unit applied to the analyte sampling analysis system shown in FIG. 3.

Referring to FIG. 4, the interface unit 200 applied to the analyte sampling analysis system includes a sample receiving unit 310 that has a space to primarily receive the sample therein from the analyte sampling apparatus 100, a sample introducing unit 320 that has a space to receive a predetermined amount of a sample from the sample receiving unit and to feed the predetermined amount of the sample into the analysis unit, a pressure supplying unit to supply pressure to receive an analyte sample in a sample loop of the sample introducing unit or pressure to transfer the sample received in the sample introducing unit to the analysis unit, and a cleaning unit including a cleaning solution feeding unit 330 to feed a cleaning solution into the sample receiving unit 310 in order to clean the sample receiving unit and/or the sample introducing unit when the sample is introduced into the analysis unit, and a draining unit 350 to drain out the cleaning solution after the sample receiving unit has been cleaned and the sample remaining in the sample receiving unit.

The sample receiving unit 310 has a space to primarily receive the sample therein from the analyte sampling apparatus. As an example, the sample receiving unit has a structure of including a cap provided at the upper portion thereof to seal the upper portion thereof and being connected with the analyte sampling apparatus by the first sample feeding line 302 passing through the cap. As another example, the sample receiving unit may be connected with another analyte sampling apparatus 100*by* the second sample feeding line 306 passing through the cap. The first sample feeding line 302 may be provided therein with a gate valve 304 to be open when the sample is transferred into the sample receiving unit, and the second sample feeding line 306 may be provided therein with a gate valve 307 to be open when the sample is transferred into the sample receiving unit. According to still another example, at least one sample receiving unit may be provided and connected with a respective sampling unit 100 for use.

Specifically, the sample receiving unit 310 is connected with a plurality of lines including an upper draining line 362, a lower draining line 352, a cleaning solution feeding line 332, sample feeding lines 302 and 306, and sample injecting lines 312 to receive the cleaning solution therein, to drain the cleaning solution, to drain the remaining sample, and to feed the sample into the sample introducing unit through relevant lines. Such moving of the sample or the cleaning solution is achieved by the selective opening/closing of the gate valves 307, 304, 333, and 323 formed in the relevant lines and the operations of pumps 354, 325, and 331 connected with the relevant lines.

As an example, although the object of the analyte sampling analysis system is to mainly monitor contaminants such as metal contained in chemicals or gas, it is significantly important to detect the variation in the concentration of the chemicals at a part having a problem during the process. Accordingly, the interface unit according to the present invention may further include a concentration analyzing unit (not shown) connected with a lower draining line 352 to measure the concentration of the sample received in the sample receiving unit 310 through the lower draining line. The concentration analyzing unit may measure the concentration in an optical manner or an electrochemical manner.

The sample introducing unit 320 includes a sample loading unit (not illustrated) connected with the sample receiving unit through the sample introducing line 312, and having the type of a switching valve having an injecting position and a loading position to receive a predetermined amount of a sample. The sample loading unit includes a sample loop 322 having a space to receive the sample. The sample loading in the sample introducing unit 320 may be achieved by filling the sample into the sample loop 322 by the operation of a pump 325 connected with the sample introducing unit after positioning the sample loop 322 having the type of the switching valve at the loading position. On the contrary, regarding to the injection of the sample into the analysis unit, the sample filled into the sample loop 322 may be transferred to the analysis unit 300 together with carrier gas or a solution as the carrier gas or the solution is injected into the sample loop 322 after the sample loop having the type of the switching value is positioned at the injecting position The pressure supplying unit includes the pump 325 coupled to one end of the sample introducing unit 320 to lower the internal pressure of the sample loop 322 when the sample loop 322 is positioned at the loading position so that the sample is introduced into the sample loop.

The cleaning unit includes a cleaning solution feeding unit 335 to feed a cleaning solution into the sample receiving unit through the cleaning solution feeding line 332 to clean the sample receiving unit and the cleaning solution draining unit 350 including the draining pump 354 to drain out the cleaning solution after the sample receiving unit has been cleaned and/or the sample remaining in the sample receiving unit through the lower draining line 352. The cleaning of the sample receiving unit is achieved to receive a next sample without contamination when the sample is injected into the analysis unit.

Specifically, the cleaning solution feeding unit 330 may clean the sample receiving unit by feeding quantitatively the cleaning solution, which is stored in a cleaning tank 335, into the sample receiving unit by the operation of the cleaning solution feeding pomp 351 and the opening of the gate valve 333. The amount of the cleaning solution that is fed may be adjusted by the level sensor 315 provided at one side of the sample receiving unit. Thereafter, if the cleaning solution is quantitatively fed, the operation of the cleaning solution feeding pump 335 is stopped and the gate valve 333 is closed. Next, the cleaning solution fed into the sample receiving unit is drained out by actuating the draining pump 354 connected with the lower drain line 352 while opening the gate valve 353. The feeding and the draining of the cleaning solution may be repeated until the internal contaminants are removed from the sample receiving unit Although not illustrated, the sample receiving unit may be significantly effectively cleaned by continuously feeding the cleaning solution into the sample receiving unit so that the cleaning solution is overflowed from the sample receiving unit. In this case, the overflowed cleaning solution may be drained out of an additional draining unit, and the cleaning solution in the sample receiving unit may be drained out by actuating the draining pump.

Figure 5:
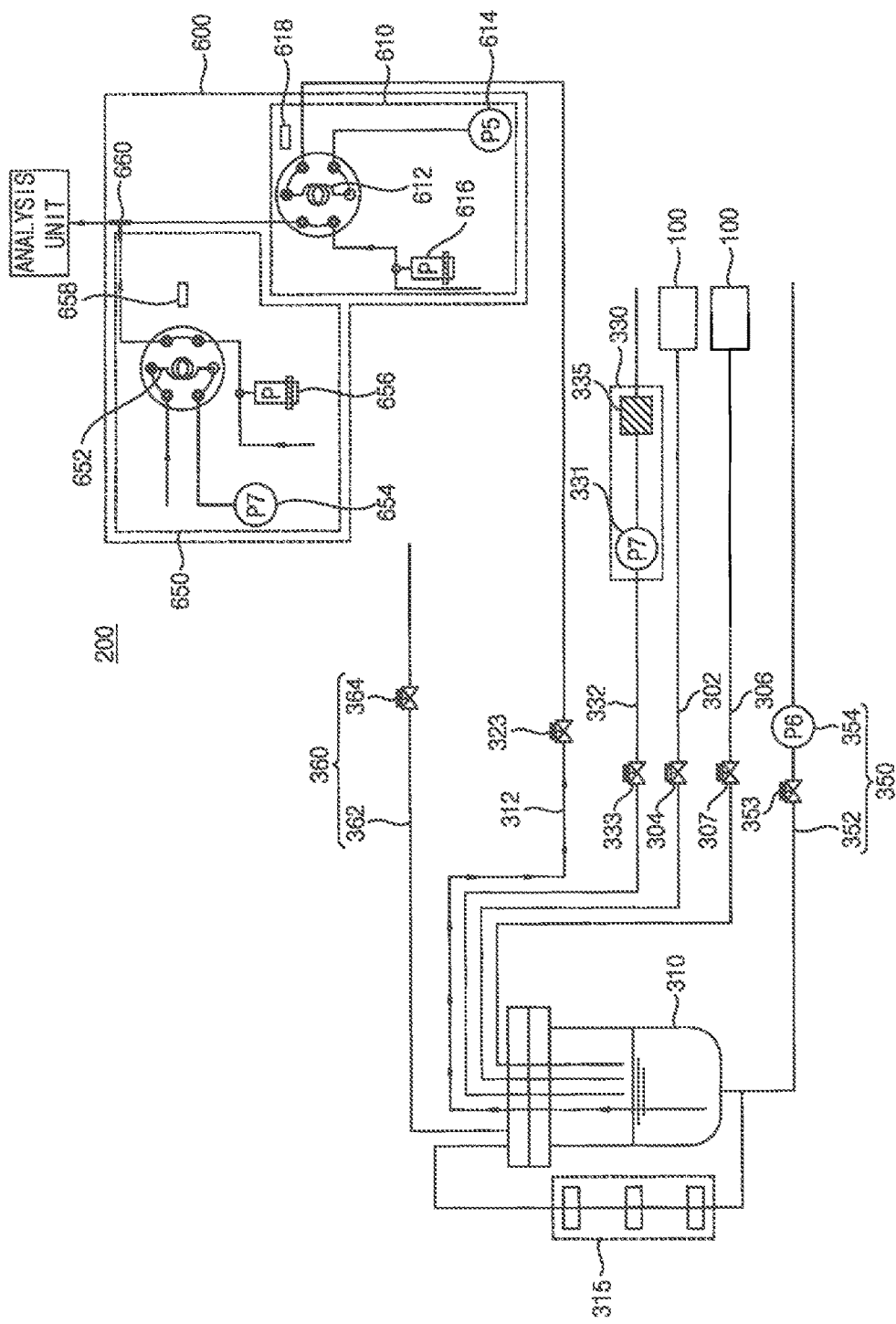
FIG. 5 is a schematic view showing a calibration interface unit applied to the analyte sampling analysis system in FIG. 3.

FIG. 5 is a schematic view showing a calibration interface unit applied to the analyte sampling analysis system in FIG. 3.

A calibration interface unit shown in FIG. 5 has a structure of substituting a calibration sample introducing unit 600 for the sample introducing unit 320 and the pressure supplying unit 352 in the interface unit 200 shown in FIG. 4. The calibration sample introducing unit 600 is applied to the calibration interface unit according to the present invention to correct errors occurring as a predetermined amount of a sample is not fed into the analysis unit when a sample introducing manner is varied depending on the type of the analysis unit.

For example, when the analysis unit is an ICP-MS, a sample is introduced through self-aspiration by a nebulizer. The rate to introduce the sample is varied depending on the characteristic of the nebulizer. Particularly, the variation in the rate to introduce the sample is greatly represented depending on the concentration or the viscosity of the chemicals. The variation exerts a serious influence on the analysis result, so that the stability of the analysis result may be degraded.

As an example, the calibration sample introducing unit 600 according to the present invention includes a sample introducing unit 610 to introduce the sample into the analysis unit at a constant rate, and a standard solution introducing unit 650 for the calibration of the sample.

The sample introducing unit 610 includes a first sample loop 612 having a space in which the sample is loaded, a first pressure pump 614 to lower the internal pressure of the first sample loop so that the sample is introduced into the first sample loop, a first metering pump 616 to feed the sample loaded into the first sample loop into the analysis unit 300 at a constant rate, and a first sensor 618 to detect whether or not the sample exists in the first sample loop. For example, the first metering pump may include a syringe pump, a diaphragm pump, a gear pump, or a piston pump. As an example, the first sample loop may be included in the sample loading unit having the type of an injection valve.

The standard solution introducing unit 650 includes a second sample loop 652 having a space in which a standard solution for calibration is loaded as the standard solution is injected, a second pressure pump 654 to lower the internal pressure of the second sample loop so that the standard solution is introduced into the second sample loop, a second metering pump 656 to feed the standard solution loaded into the second sample loop into the analysis unit at a constant rate, and a second sensor 658 to detect whether or not the sample exists in the first sample loop.

As an example, the first metering pump or the second metering pump may include a syringe pump, a diaphragm pump, a gear pump, or a piston pump. For example, the second sample loop may be included in the sample loading unit having the type of an injection valve.

The sample introducing unit 610 and the standard solution introducing unit 650 in the calibration sample introducing unit 600 is connected with the analysis unit 300 by a T-shaped line 660. Accordingly, the sample fed into the analysis unit from the sample introducing unit and the standard solution fed into the analysis unit from the standard solution introducing unit are mixed together in the T-shaped line 660 and fed into the analysis unit. A dilution of the standard solution fed into the analysis unit may be varied depending on an amount of analyte sample.

The standard solution used for the calibration of the analysis unit includes an extremely-low concentration of a standard solution. In this case, the standard solution is chemically changed, so that errors may occur in measurement. Therefore, according to the present invention, the following manners may be performed to make a calibration curve by diluting a higher concentration of a standard solution to various concentrations by employing the calibration sample introducing unit 600

First, the standard solution is loaded into the second sample loop by pressure supplied from the second pressure pump 654.

Thereafter, after adjusting the position of the second sample loop through the switching of the loading unit, the standard solution loaded into the second sample loop is introduced the T-shaped line 660 connected with the analysis unit using the second metering pump 656. In this case, the sample loaded into the first sample loop is fed into the T-shaped line, which is connected with the analysis unit, along with the standard solution by the first metering pump. The standard solution and the sample fed into the T-shaped line may be mixed together in the T-shaped line and introduced into the analysis unit.

The calibration sample introducing unit 600 having the above configuration may enables the calibration for the analysis unit by using the variation in the dilution ratio of the mixture solution of the standard solution and the sample to be fed into the analysis unit according to the variation in an amount of the standard solution. Through the calibration of the analysis unit, the calibration curve of the standard solution may be made using the analysis unit, so that the sample can be analyzed with more precision.

DESCRIPTION OF REFERENCE NUMERALS

100: analyte sampling apparatus  170: analyte sample introducing unit
160: trapping solution feeding    120: spray unit -continued

| | |
|---|---|
| unit | |
| 130: spray chamber | 140: trapping tube |
| 110: trapping container | 180: sample transfer unit |
| 200: interface unit | 300: analysis unit |
| 400: control unit | 500: analyte sampling analysis system |
| 600: calibration sample introducing unit | |

The invention claimed is:

1. An analyte sampling method comprising:
1) primarily trapping an analyte material, which is contained in an analyte sample, in a trapping solution of an aerosol state by mixing and spraying a predetermined amount of the trapping solution and the analyte sample in an aerosol state using a spray unit;

2) secondarily trapping the analyte material in the trapping solution by mixing the aerosol-state trapping solution having the analyte material primarily trapped therein with the analyte material, which is not trapped, in a trapping tube;

3) trapping the trapping solution having the analyte material secondarily trapped therein in a trapping container; and 4) feeding the trapping solution having the analyte material finally trapped therein into an analysis unit through a sample feeding line, wherein, when the analyte sample is in a gas phase, performing followings by at least one time after step 3):

tertiarily trapping an analyte material contained in an analyte sample in the trapping solution of the aerosol state by mixing and spraying a predetermined amount of the analyte sample newly fed and the trapping solution having the analyte material secondarily trapped therein using the spray unit, quaternarily trapping the analyte material in the trapping solution by mixing the analyte sample with the aerosol-state trapping solution having the analyte material tertiarily trapped therein in a trapping tube, and trapping the trapping solution having the analyte material quaternarily trapped therein in the trapping container.

2. The analyte sampling method of claim 1, further comprising:

cleaning the trapping container by feeding a cleaning solution into the trapping container to remove a remaining contaminant from the trapping container; and draining out the cleaning solution received in the trapping container through the sample feeding line, before step 1) or after step 4).

3. An analyte sampling analysis system comprising:

a spray unit to receive a trapping solution and an analyte sample, and to mix and spray the analyte sample and the trapping solution of an aerosol state together; a spray chamber to provide a space to primarily trap an analyte material, which is contained in the analyte sample, in the trapping solution of the aerosol state; a trapping tube to secondarily trap the analyte material, which is not trapped in the spray chamber, by receiving the analyte sample and the trapping solution of the aerosol state from the spray chamber and mixing the trapping solution with the analyte sample; a trapping container to receive the trapping solution having the analyte material trapped therein through the trapping tube; and a sample transfer unit to feed purge gas into the trapping container to transfer the tapping solution having the analyte material tapped therein to an analysis unit through a sample transfer line by the purge gas;

an interface unit comprising a sample introducing unit or a calibration sample introducing unit to receive a sample from the analyte sampling apparatus and to feed a predetermined amount of a sample into an analysis unit;

the analysis unit to receive the predetermined amount of the sample from the interface unit and to analyze a type and a content of an analyte material contained in the sample; and a control unit to control operations of elements of the analyte sampling apparatus and the interface unit and an operation of the analysis unit.

4. The analyte sampling analysis system of claim 3, wherein the interface unit further comprises:

a sample receiving unit having a space to primarily receive the sample therein from the analyte sampling apparatus;

a sample introducing unit having a space to receive the predetermined amount of the sample such that the predetermined amount of the sample received in the sample receiving unit is fed into the analysis unit;

a pressure supplying unit to supply pressure to receive the sample in the sample introducing unit or to inject the sample received in the sample introducing unit to the analysis unit; and a cleaning unit including a cleaning solution feeding unit to feed a cleaning solution into the sample receiving unit such that the sample receiving unit is cleaned when the sample is introduced into the analysis unit, and a draining unit to drain out the cleaning solution and the sample remaining in the sample receiving unit after the sample receiving unit is cleaned.

5. The analyte sampling analysis system of claim 3, wherein the interface unit further comprises a concentration analyzing unit connected with a lower draining line connected with a lower portion of a sample receiving unit to receive the sample from the sample receiving unit through the lower draining line such that concentration of the sample is measured.

6. The analyte sampling analysis system of claim 3, wherein the interface unit further comprises:

a sample receiving unit having a space to primarily receive the sample from the analyte sampling apparatus;

a calibration sample introducing unit comprising a sample introducing unit and a standard solution introducing unit to feed a predetermined amount of a sample, which is received in the sample receiving unit, into the analysis unit and to feed a standard solution for performing calibration of the analysis unit, respectively; and a cleaning unit comprising a cleaning solution feeding unit to feed a cleaning solution into the sample receiving unit such that the sample receiving unit is cleaned when the sample is introduced into the analysis unit, and a draining unit to drain out the cleaning solution or a sample remaining in the sample receiving unit after the sample receiving unit is cleaned.

* * * * *